United States Patent [19]

Flemer, III

[11] Patent Number: Plant 5,730

[45] Date of Patent: Apr. 29, 1986

[54] FLOWERING CHERRY TREE

[75] Inventor: William Flemer, III, Princeton, N.J.

[73] Assignee: Treesearch, Kingston, N.J.

[21] Appl. No.: 664,203

[22] Filed: Oct. 24, 1984

[51] Int. Cl.[4] ..... A01H 5/03

[52] U.S. Cl. ..... Plt./37

[58] Field of Search ..... Plt./37

*Primary Examiner*—Robert E. Bagwill

*Attorney, Agent, or Firm*—Frank B. Robb

[57] ABSTRACT

A flowering cherry tree selected as a seedling in a block of open pollinated variety *Prunus yedoensis* "Akebono", (unpatented) distinguished from "Akebono" by the strong pink color of its abundant flowers when fully open, "Akebono" flowers being pale pink by comparison, the variety hereof being vigorous with spreading growth broader than tall, the flower buds being resistant to freezing, blooming abundantly when regular "Akebono" trees lost as much as ninety percent of buds due to freezing, and the bark showing no injury to minus 19 degrees F.

2 Drawing Figures

1

My present invention relates to a new and distinct variety of flowering cherry tree which was discovered as a seedling in a block of *Prunus yedoensis* "Akebono" (an unpatented variety), the "Akebono" variety being grown in substantial numbers in a nursery in the vicinity of Plainsboro Township, N.J.

I have carried on the development of flowering fruit trees for many years and am thus able to recognize what seems to be an outstanding improvement in the flowering cherry variety for a number of reasons, and particularly in this instance because of the distinctive strong pink color of the abundant flowers which are produced by this particular variety.

This strong pink color contrasts with the usual pale pink color of the *Prunus yedoensis* variety "Akebono" and because of this strong pink color I have chosen to call the same *Prunus yedoensis* "Afterglow", which appears to be suitably fitting, and appropriate therefore.

In addition to the foregoing, after growing the seedling by bud grafting to carry out the necessary asexual reproduction thereof, have found that it does in fact reproduce true to form and the characteristics found are present in succeeding generations as propagated.

Additional aspects of the variety which I believe make the same attractive are the vigorous, spreading, broader than tall habit of the tree which has been consistently the case, with rapid growth likewise being present and even more desirable aspect perhaps, the resistance to cold damage of the buds which will withstand temperatures and have withstood temperatures to −19 degrees F. without noticeable damage, in contrast to other usual *Prunus yedoensis* trees which suffer bud damage such as to lose 90% of their buds, as well as bark injury from freezing, which does not occur in the instant variety.

Figure 1:
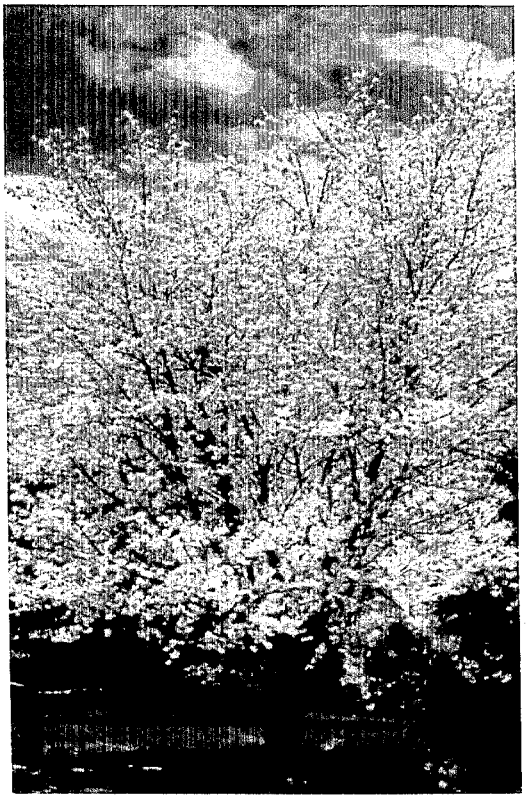
Figure 2:
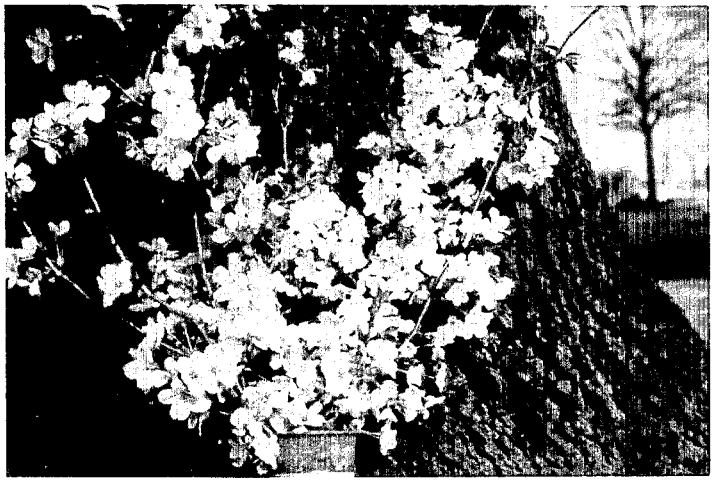

As will be observed from the drawing which is attached hereto and forms a part hereof, FIG. 1 being a view of a tree showing the colors as they appear in a whole tree and FIG. 2 comparing the branches of a tree as in FIG. 1 with the parent "Akebono" which is of course a white color in appearance, all of the colors and the trees and branches being set forth in color as nearly representative of the color which is the primary characteristic as is possible to make the same in an illustration

2 of this kind and to reproduce the same for consideration.

There follows a detailed description of my new variety with color terminology in accordance with the Munsell Color Chart, published by Munsell Color Company, Inc. and known as the Nickerson Color Fan, except where general color terms of ordinary dictionary significance may be applicable and according to my personal observations and judgment in the use of such color designations as compared with the color chart referred to.

Parentage: Seedling.

*Seed parent.*—*Prunus yedoensis* "Akebono". (an unpatented variety).

*Pollen parent.*—Unknown.

Propagation: Holds its distinguishing characteristics through succeeding propagations by bud-grafting.

Locality where grown and observed: Plainsboro Township, N.J.

Tree: Medium size; spreading; low; hardy.

*Trunk.*—Stocky; smooth.

*Branches.*—Slender; smooth.

*Color.*—Moderate yellowish brown; Munsell Color 10 YR 4/4.

*Lenticels.*—Moderately abundant. Number — 4 to 5 per cm. of twig.

Foliage:

*Leaves.*—Abundant. Size — Length 12 to 13 cm. Width 4.5 to 5 cm. Shape — Oval; acuminate. Color — Upper Surface Moderate olive green, Munsell Color 2.5 GY 4/3. Lower Surface Dark yellow green, Munsell Color 5 GY 5/6. Margin — Serrate. Petiole — Short (2 to 2.5 cm. long). Glands — Average number 1 to 2 per leaf; opposite flattened. Stipules — None.

Flower buds: Very hardy to −19 degrees F.

*Size.*—0.4 cm. long.

*Shape.*—Narrowly oval, pointed tip.

*Color.*—Moderate reddish brown, Munsell Color 2.5 YR 3/3.

Flowers:

*Blooming season.*—First bloom April 10 to 15; Full bloom April 15 to 17.

*Quantity.*—Abundant; borne in clusters of 4 to 6 flowers.

*Size.*—Large; 4 cm. wide; stems 3 cm. long.

Petalage:

*Number of petals.*—Five.

*Shape of petals.*—Oval with notched tips; depth of notch 0.2 cm.

*Size of petals.*—Length 2 cm. Width 1.5 cm.

*Color.*—Buds — Deep purplish pink Munsell Color 7.5 RP 6/12. Fully open petals — Strong pink Munsell Color 2.5 R 7/8. Tips of stamens — Dark orange yellow Munsell Color 7.5 YR 6/9.

Fruits:

*Borne.*—Early July.

*Quantity.*—Moderately abundant.

*Size.*—About 1.2 cm. long, rounded.

*Color.*—Purple black.

I claim:

1. A new and distinct variety of flowering cherry tree substantially as herein shown and described, characterized particularly as to novelty by the unique combination of the strong pink color of its abundant flowers, vigorous, spreading, broader than tall habit, rapid growth, resistance to cold damage to buds, withstanding temperatures to minus nineteen degrees F., in contrast to other usual *Prunus yedoensis* trees which suffer bud damage such as to lose ninety percent of their buds and bark injury from freezing.

* * * * *